United States Patent
Kumagai et al.

(10) Patent No.: US 9,315,584 B2
(45) Date of Patent: Apr. 19, 2016

(54) LH-TYPE BISPECIFIC ANTIBODY

(75) Inventors: Izumi Kumagai, Sendai (JP); Ryutaro Asano, Sendai (JP); Mitsuo Umetsu, Sendai (JP)

(73) Assignee: TOHOKU UNIVERSITY, Sandai-Shi (JP)

( * ) Notice: Subject to any disclaimer, the term of this patent is extended or adjusted under 35 U.S.C. 154(b) by 1136 days.

(21) Appl. No.: 13/257,614

(22) PCT Filed: Jan. 4, 2010

(86) PCT No.: PCT/JP2010/050008
§ 371 (c)(1),
(2), (4) Date: Nov. 15, 2011

(87) PCT Pub. No.: WO2010/109924
PCT Pub. Date: Sep. 30, 2010

(65) Prior Publication Data
US 2012/0095191 A1      Apr. 19, 2012

(30) Foreign Application Priority Data

Mar. 25, 2009 (JP) ................................ 2009-075050
Nov. 16, 2009 (JP) ................................ 2009-260576

(51) Int. Cl.
*A61K 39/00* (2006.01)
*C07K 16/18* (2006.01)
*C07K 16/46* (2006.01)
*C07K 16/28* (2006.01)

(52) U.S. Cl.
CPC ............. *C07K 16/46* (2013.01); *C07K 16/2809* (2013.01); *C07K 16/2863* (2013.01); *C07K 2317/24* (2013.01); *C07K 2317/31* (2013.01); *C07K 2317/626* (2013.01)

(58) Field of Classification Search
None
See application file for complete search history.

(56) References Cited

U.S. PATENT DOCUMENTS 7,635,475 B2    12/2009    Kumagai et al.
2009/0202532 A1    8/2009    Kumagai et al.

FOREIGN PATENT DOCUMENTS

JP    2004-242638 A    9/2004
WO    WO 2007/108152 A1    9/2007

OTHER PUBLICATIONS

MacCallum et al. (1996). J. Mol. Biol. 262:732-745.*
De Pascalis et al. (2002). Journal of Immunology. 169:3076-3084.*
Rudikoff et al. (1982). PNAS. 79:1979-1983.*
International Search Report, dated Feb. 16, 2010, issued in PCT/JP2010/050008.
Lu et al., "The effect of variable domain orientation and arrangement on the antigen-binding activity of a recombinant human bispecific diabody", Biochemical and Biophysical Research Communications, vol. 318, No. 2, pp. 507-513, May 28, 2004.
Todorovska et al., "Design and application of diabodies, triabodies and tetrabodies for cancer targeting", Journal of Immunological Methods, vol. 248, No. 1-2, pp. 47-66, Feb. 1, 2001.

* cited by examiner

*Primary Examiner* — Christine J Saoud
*Assistant Examiner* — Jon M Lockard
(74) *Attorney, Agent, or Firm* — Birch, Stewart, Kolasch & Birch, LLP

(57) ABSTRACT

Provided are a novel diabody type bispecific antibody, the function of which as a bispecific antibody is improved to provide a higher additional value, such as cost saving caused by a reduction in dose, to a drug; and a method for producing the same. A humanized diabody type bispecific antibody (LH-diabody type bispecific antibody) characterized in that an L-chain is located in the N-terminal side in each polypeptide (LH type); a humanized high-functional bispecific antibody which contains said LH diabody type bispecific antibody; a nucleic acid molecule encoding both of two kinds of single-stranded polypeptides constituting said bispecific antibody; and a method for producing said antibody which comprises culturing a host cell having been transformed by an expression vector containing said nucleic acid molecule.

11 Claims, 7 Drawing Sheets

LH-TYPE BISPECIFIC ANTIBODY

FIELD OF THE INVENTION

The present invention is related to a humanized diabody-type bispecific antibody (LH-type) that is characterized in that a variable region of a light chain is located in the N-end (N-terminal) side of each polypeptide constituting the bispecific antibody, and a humanized highly functional bispecific antibody comprising said LH-diabody type bispecific antibody, (both of which are referred to as "LH-type bispecific antibody"), and a single-chain (single-stranded) polypeptide constituting the antibody, a nucleic acid encoding the polypeptide, a method for the production of the antibody, and a pharmaceutical composition comprising them.

BACKGROUND OF THE INVENTION

Recently, immunotherapy has been used as a safe therapy for the treatment of cancer, rheumatoid, etc. In the immunotherapy of cancer, an antibody showing a cytotoxic activity specifically upon cancer cells is used. While it is recognized that an antibody drug comprising such antibody will show high and safe therapeutic effects with little side effects, it has a problem that it would cost much since said drug needs to be produced by using established animal cells.

As a result, it has been a worldwide trend to produce a low molecular-weight antibody such as a single-chain antibody (scFV) that contains VH and VL of a certain antibody in a single-chain polypeptide. Such low molecular-weight antibody can be economically produced by E. coli. However, it is concerned that its half life in a body will be decreased due to its low molecular weight, reducing the period of effecting medical benefits. Also, it is a problem that affinity of such low molecular-weight antibody with monovalence is lower than that of a full antibody such as IgG with polyvalence for a target antigen. Furthermore, as a main mechanism of an action of the antibody drug is considered to be an antibody dependent cytotoxic activity (ADCC) via Fc region, it is concerned that the ADCC of the scFv that has no Fc region would be low. Non-Patent Document 1 may be referred to with respect to the scFv.

Accordingly, a bispecific antibody with a low molecular weight has been developed, which can cross-link between cancer cells and immune cells. Only one of such bispecific antibody with a low molecular weight, called "BiTE", which consists of two fragments of scFv linked with each other in tandem, has been now brought into a clinical trial (Science 2008 Aug. 15:321 (5891): 974-7). However, as the BiTE is produced by using animal cells, its production cost and yield have become problematic. Furthermore, it was reported that it was difficult to prepare the tandem scFv-type bispecific antibody with a low molecular weight such as BiTE from soluble fraction of E. coli (J Mol Biol, 2003 330(1):99-111).

Among antibodies with multiple specificities, an antibody with bispecificity (Bispecific Antibody: BsAb) has been studied intensively. The bispecific antibody can bind specifically to two different kinds of antigens so that it will be utilized as a therapeutic agent having a specific anti-cancer effect. A diabody (Db) is a minimum unit of the above bispecific antibody. It was developed by utilizing the property that the variable region in a heavy chain (VH) and the variable region in a light chain (VL) derived from the same parent antibody will form a hetero-dimer through non-covalent bond (Non-Patent Document 2).

The diabody-type bispecific antibody is characterized by having low immunogenicity and high infiltrating activity into tumor tissues due to its low molecular weight (ca. 60,000), and by being able to be easily mass-produced at a low cost with use of microorganisms such as E. coli, and to be easily altered in function by means of genetic engineering.

The present inventors already found that the diabody-type bispecific antibody (Ex3) that was produced by utilizing an anti-human EGF receptor 1 (Her 1) antibody 528 and an anti-CD3 antibody OKT3, and its humanized diabody-type bispecific antibody (referred to as "hEx3" in Patent Document 1) showed extremely strong anti-tumor effects. It was further speculated that the structural stability of the variable regions of the above antibodies 528 and OKT3 themselves and their combination are very important for showing such advantageous effects by comparison with an diabody-type bispecific antibody prepared using other antibodies.

Furthermore, the present inventors have developed a highly functional bispecific antibody based on said humanized diabody-type bispecific antibody (Patent Document 2).

Methods for the production of bispecific antibodies other than the diabody-type bispecific antibody are described in Non-Patent Documents 3 and 4.

Patent Document 1: Japanese Patent No. 3803790
Patent Document 2: WO 2007/108152 A1
Non-Patent Document 1: Rosenburg and Moore (Ed.), "The Pharmacology of Monoclonal Antibodies", Vol. 113, Springer-Verlag, New York, pp. 269-315 (1994)
Non-Patent Document 2: Hollinger, et al., Proc. Natl. Acad. Sci. USA 90, 6444-6448, 1993
Non-Patent Document 3: Alt, M., et. al. Novel tetravalent and bispecific IgG-like antibody molecules combining single-chain diabodies with the immunoglobulin gammal Fc or CH3 region. FEBS Lett., 454, 90-4. (1999)
Non-Patent Document 4: Lu, D., et. al. A fully human recombinant IgG-like bispecific antibody to both the epidermal growth factor receptor and the insulin-like growth factor receptor for enhanced antitumor activity. J Biol Chem., 280, 19665-72. (2005)

DISCLOSURE OF THE INVENTION

Problem to be Solved by the Invention

Although the diabody-type bispecific antibody such as "Ex3" has an excellent activity, its production efficiency has been as low as a few mg/L of culture medium at least in a basic research level since it is prepared by expression in E. coli, followed by winding-off from an insoluble fraction (Biochem Soc Trans, 2002 30(4):507-11). It is therefore desired to provide higher functions with the diabody-type bispecific antibody in order to reduce a administration dose and to enhance added values as a drug such as a low cost.

Means for Solving the Problems

The present inventors have studied to resolve the above problems and developed a humanized diabody-type bispecific antibody that is characterized in that a variable region of the light chain is located in the N-end (N-terminal) side of each polypeptide constituting the bispecific antibody (LH-diabody type bispecific antibody: LH-type Ex3), and a method for a preparation of said bispecific antibody from E. coli, especially from its soluble fraction, leading to the present invention. Furthermore, it was confirmed by the present inventors that such a humanized highly functional bispecific antibody as those in Patent Document 2 that has been constructed using said LH-type antibody showed a higher cytotoxic activity.

The present invention is therefore related to the following aspects:

[1] A diabody-type bispecific antibody consisting of a first polypeptide comprising a humanized variable region of the light chain (5L) of an anti-human EGF receptor 1 antibody 528 and a humanized variable region of the heavy chain (OH) of an anti-CD3 antibody OKT in this order from its N-end to C-end; and a second polypeptide comprising a humanized variable region of the light chain (OL) of an anti-CD3 antibody OKT and a humanized variable region of the heavy chain (5H) of an anti-human EGF receptor 1 antibody 528 in this order from its N-end to C-end.

[2] A humanized highly functional bispecific antibody comprising humanized variable regions of the heavy chain (5H) and the light chain (5L) of an anti-human EGF receptor 1 antibody 528, and humanized variable regions of the heavy chain (OH) and the light chain (OL) of an anti-CD3 antibody OKT3; and having one of the following structures:

(i) (5LOH)-(a peptide linker)-(OL5H) or (OL5H)-(a peptide linker)-(5LOH);

(ii) an antibody wherein a humanized diabody-type bispecific antibody consisting of two kinds of the single-chain polypeptides of (5LOH) and (OL5H) is bonded to two Fc regions of a human antibody via each hinge region through either of the two single-chain polypeptides;

(iii) an antibody wherein the single-chain polypeptide of (5LOH)-(a peptide linker)-(OL5H) or (OL5H)-(a peptide linker)-(5LOH) is bonded to two Fc regions of a human antibody via each hinge region.

[3] The humanized highly functional bispecific antibody of the aspect [2] having the structure (ii), wherein the humanized diabody-type bispecific antibody is bonded to the hinge regions via a protease cleavage site.

[4] The humanized highly functional bispecific antibody of the aspect [2] having the structure (iii), wherein the single-chain polypeptide is bonded to the hinge regions via a protease cleavage site.

[5] The diabody-type bispecific antibody of the aspect [1] or [2] wherein the humanized variable region of the light chain and the humanized variable region of the heavy chain are linked via a peptide linker in the single-chain polypeptide.

[6] A bispecific antibody of any one of the aspects [1]-[5] wherein the 5L, 5H, OL and OH have an amino acid sequence represented by SEQ ID NOS: 2, 4, 6 and 8, respectively.

[7] A single-chain polypeptide constituting the bispecific antibody of any one of the aspects [1]-[6].

[8] A nucleic acid molecule encoding the single-chain polypeptide of the aspect [7].

[9] A nucleic acid molecule encoding both of the two kinds of the single-chain polypeptides constituting the bispecific antibody of any one of the aspects [1]-[6].

[10] A replicable cloning vector or an expression vector containing the nucleic acid molecule of the aspect [8] or [9].

[11] The vector of the aspect [10], which is a co-expression vector.

[12] The vector of the aspect [10] or [11], which is a plasmid vector.

[13] A host cell transformed with the vector of any one of the aspects [10]-[12].

[14] The hose cell of the aspect [13], which is a prokaryotic cell.

[15] The hose cell of the aspect [14], which is E. coli.

[16] A method for the production of the bispecific antibody of any one of the aspects [1]-[6], comprising culturing a host cell according to any one of the aspects [13]-[15] to express the two kinds of the single-chain polypeptides constituting said bispecific antibody, collecting and purifying said single-chain polypeptides, assembling the two kinds of the single-chain polypeptides, and separating and collecting the bispecific antibody thus formed.

[17] The method of the aspect [16] wherein the host cell is E. coli, and the two kinds of the single-chain polypeptides are collected from supernatant of a culture medium, periplasm fraction, intracellular soluble fraction or intracellular insoluble fraction.

[18] A method for the production of the bispecific antibody of any one of the aspects [1]-[6], comprising culturing a host cell transformed with the co-expression vector of the aspect [11] to express the two kinds of the single-chain polypeptides constituting said bispecific antibody, allowing the transformed cell to form the diabody-type bispecific antibody in said cell, and separating and collecting the bispecific antibody thus formed.

[19] A method for the production of the humanized diabody-type bispecific antibody consisting of two kinds of the single-chain polypeptides of (5L OH) and (OL511) or the humanized highly functional bispecific antibody of the aspect [2] having the structure (i), comprising digesting the humanized highly functional bispecific antibody of the aspect [3] or [4] with a protease to cleave the Fc region and the hinge region.

[20] A pharmaceutical composition comprising the bispecific antibody of any one of the aspects [1]-[6] as an active ingredient.

[21] The pharmaceutical composition of the aspect [20] for use in eliminating, hurting, damaging and/or reducing tumor cells.

Advantages of the Invention

The LH-diabody type bispecific antibody according to the present invention shows a very high cytotoxic activity comparable to that of the IgG-lke highly functional bispecific antibody (Ex3-scDb-Fc: Patent Document 2) that consists of the humanized diabody-type bispecific antibody (Ex 3) fused to Fc. According to the method of the present invention, the antibody can be produced from the soluble fraction of the bacteria in an amount of twice or more than that of conventional bispecific antibodies. Furthermore, the humanized highly functional bispecific antibody constructed on the basis of the LH-type bispecific antibody (LH type BsAb) shows much higher cytotoxic activity than that of LH-diabody type bispecific antibody.

BEST MODE FOR CARRYING OUT THE INVENTION

Figure 1:
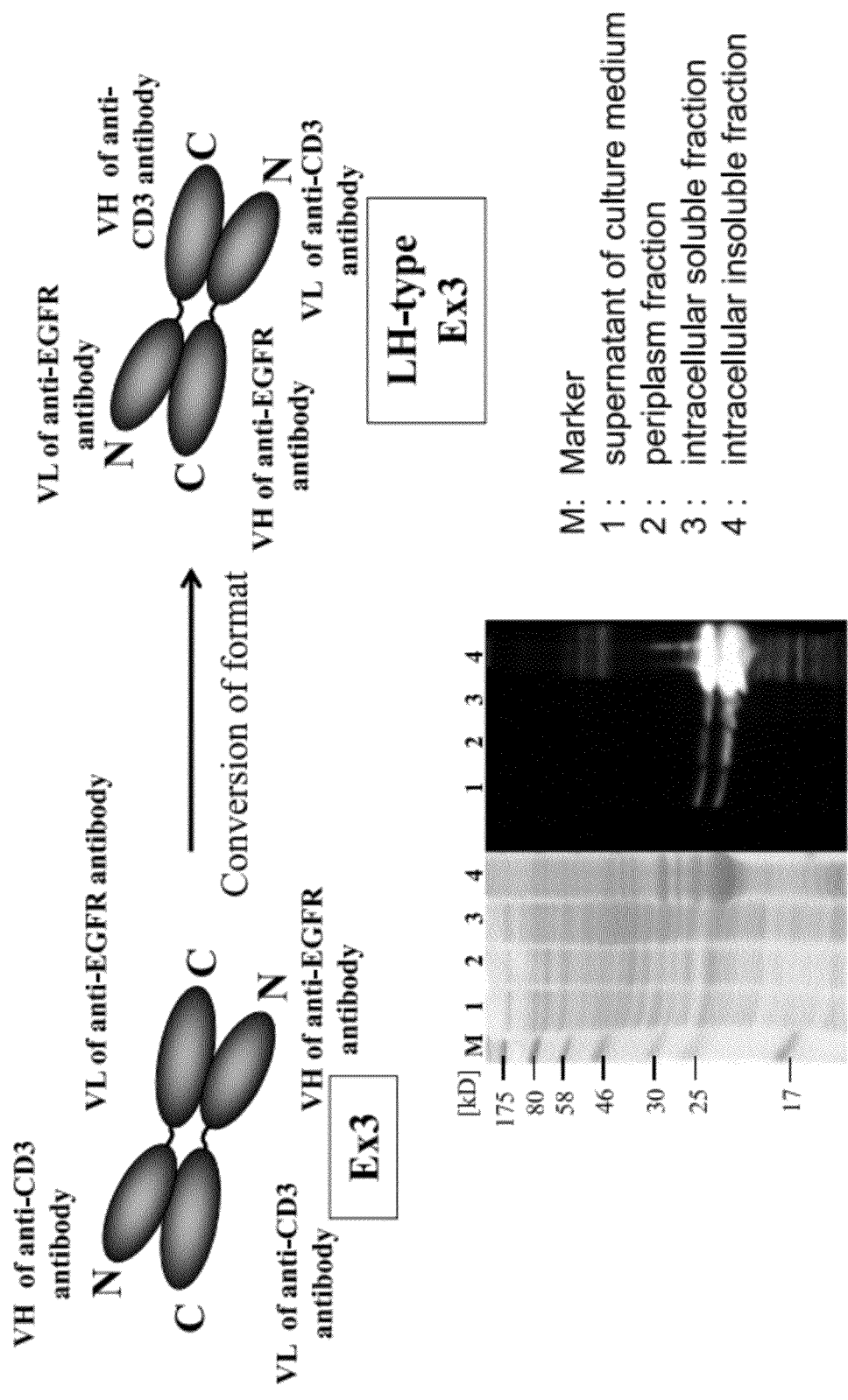
FIG. 1 shows the results of preparation of the LH-diabody type bispecific antibody from the supernatant of culture medium of E. coli. and the intracellular fractions of E. coli.
Figure 2:
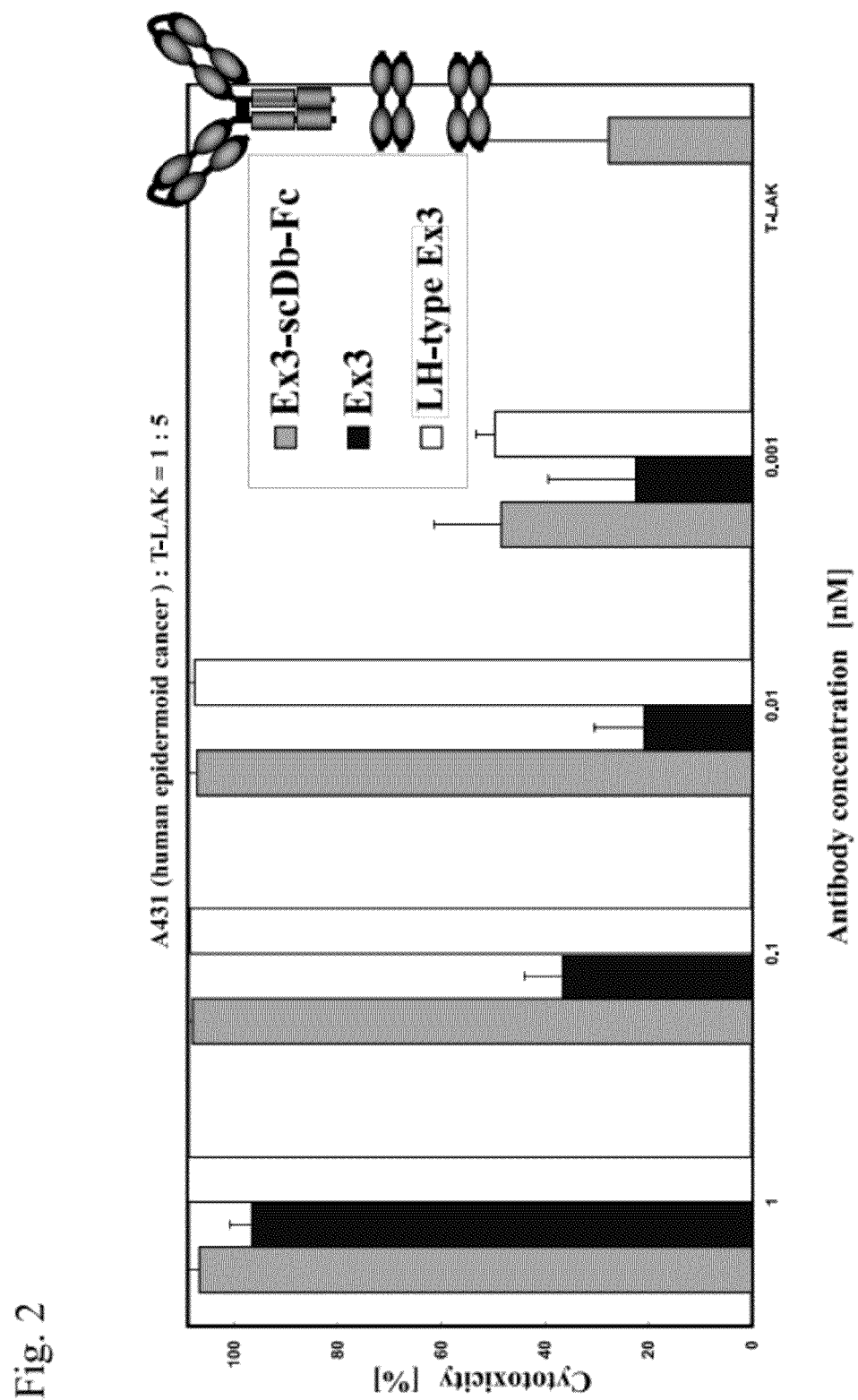
FIG. 2 shows the results of Cytotoxicity Test (cell-growth inhibition test) on human epidermoid cancer cell, A431 (ATCC No. CRL-1555) with the LH-diabody type bispecific antibody (LH-type Ex3), the humanized Ex3 disclosed in Patent Document 1 and Ex3-scDb-Fc disclosed in Patent Document 2.

Mouse B cell hybridoma 528 producing anti-EGFR antibody (ID:TKG0555) is deposited in Cell Resource Center for Biomedical Research, Institute of Development, Aging and Cancer, TOHOKU University. The above hybridoma 528 producing anti-EGFR antibody is also stored at ATCC with an ATCC Accession No. HB-8509, so that may be obtained from these deposit authorities.

On the other hand, the anti-CD3 antibody, OKT3 (ID: TKG0235) is deposited in Cell Resource Center for Biomedical Research, Institute of Development, Aging and Cancer, TOHOKU University, and is also stored at ATCC with an ATCC Accession No. CRL-8001, so that it may be obtained from these deposit authorities.

cDNA may be prepared by known methods. For example, mRNA is extracted with ISOGEN (Nippon Gene Co.) and then cDNA is prepared by means of First-Strand cDNA Synthesis Kit (Amersham Biosciences Co.). PCR reaction is done for the cDNA using cloning primers that are synthesized in accordance with the disclosure of a Reference document (Krebber, A. et al. Reliable cloning of functional antibody variable domains from hybridomas and spleen cell repertoires employing a reengineered phage display system. J Immunol Methods 201, 35-55. (1997)) so as to determine the sequences of the variable regions of H and L chains of each antibody.

The term "humanized" variable region as used herein means a human immunoglobulin (a recipient antibody) in which at least a part of the residues of complementary-determining region (CDR) is replaced with residues derived from the CDR of a non-human animal antibody (a donor antibody) that has a desired specificity, affinity and capability, such as those of mouse, rat, and rabbit. In some cases, the residue(s) of a Fv framework (FR) in the human immunoglobulin is replaced with residue(s) of the corresponding non-human antibody. The humanized antibody may further comprise a residue that is not found in the recipient antibody or the introduced CDR or framework. These changes are made in order to optimize or improve the properties of the resulting antibody. More detailed information on these changes are referred to Jones et al., Nature 321, 522-525 (1986); Reichmann et al., Nature 332, 323-329 (1988); EP-B-239400; Presta, Curr. Op. Struct. Biol 2, 593-596 (1992); and EP-B-451216.

The humanized variable region of the antibody may be prepared in accordance with any methods known to those skilled in the art, for example, by analyzing various conceptual humanized preparations based on three-dimensional immunoglobulin models of the recipient antibody and donor antibody, and analyzing them. The three-dimensional immunoglobulin models are well known in the art, being referred to, for example, WO92/22653.

Thus, one example of the humanized variable region according to the present invention is an antibody wherein the complementary determining regions (CDR) in the variable regions are derived from a mouse antibody, and the other parts are derived from a human antibody.

The activity or function of the resulting antibody may be deteriorated due to the humanization. The activity or function of the diabody-type bispecific antibody according to the present invention may be therefore improved by being provided with a site-specific mutation at an appropriate position in the single-chain polypeptide, for example, at a position in the framework which can affect the CDR structure, such as in canonical sequence or vernier sequence.

Specifically, the humanization of the variable regions of 528 was performed by means of CDR grafting. Thus, a human antibody having FR (Frame Work) with the highest homology was screened and selected by a homology search in view of the length of each CDR and the like. An amino acid sequence was designed, in which the CDR of the selected human antibody was replaced with CDR of 528. The total gene may be then synthesized by means of overlapping PCR by preferably using the optimum codons for E. Coli.

It was already reported that the variable region of the humanized OKT3 could maintain its activity when compared with the mouse OKT3 (Adair, J. R. et al. Humanization of the murine anti-human CD3 monoclonal antibody OKT3. Hum Antibodies Hybridomas 5, 41-7. (1994)). The total gene was synthesized by means of overlapping PCR based on the amino acid sequence of the variable regions of the humanized OKT3 disclosed in the above document. The optimum codons for E. coli were used in the synthesis. It was also reported that the use of the gene containing the optimum codons would increase the expression level in E. coli.

The humanized variable region of the light chain (5L) and the humanized variable region of the heavy chain (5H) of the anti-human EGF receptor 1 antibody 528, and the humanized variable region of the light chain (OL) and the humanized variable region of the heavy chain (OH) of the anti-CD3 antibody OKT, which are comprised in the single-chain polypeptides that constitute the LH-diabody type bispecific antibody consisting of the present invention may have a nucleotide sequence and an amino acid sequence represented by SEQ ID NOS:1 and 2, 3 and 4, 5 and 6, and 7 and 8, respectively.

It is preferred that the humanized variable regions of the light chain (VL) and the heavy chain (VH) are linked via an appropriate peptide linker. Any linker known in the art or one modified therefrom may be optionally selected and used in the present invention as long as it makes hard for the single-chain polypeptide to interact within its molecule so that it will enable the formation of a polymer of plurality of the single-chain antibodies. As a result, the VH and VL derived from different single-chain antibodies with each other shall assemble appropriately so as to form a structure that mimics or improves the function of an original protein (the function originated or derived from the original polypeptide or protein) such as all or part of its biological activity. The peptide linker according to the present invention may have about 1-20 amino acids, preferably about 1-15 amino acids, more preferably about 2-10 amino acids.

Alternatively, it is preferable that two humanized variable regions may be directly linked with each other in the single-chain polypeptide. In such case, one or a few amino acids located at C-end of the humanized variable regions of the light chain (VL), or one or a few amino acids located at N-end of the humanized variable regions of the light chain (VH) are deleted in order to increase three-dimensional degree of freedom in each single-chain antibody and to improve their polymerization.

The polypeptide having an amino acid sequence in which one or a few amino acids are substituted, deleted, inserted or added in the amino acid sequences represented by the above SEQ ID NOS, and having substantially the same property and function as that of the original polypeptide such as an antigen specificity as that of its variable region may be also used as a polypeptide constituting the present LH-type BsAb. it is preferable to make a substitution among amino acids belonging to the same group (polar, non-polar, hydrophobic, hydrophilic, positive-charged, negative-charged, or aromatic amino acid group), or to make a deletion or addition of amino acid so as not to cause a substantial difference or effects with respect to the three-dimensional or local charge-condition of the protein. Such polypeptides having the substitution, deletion or addition of the amino acid(s) my be easily prepared by well known methods such as site-specific mutation (point mutation method or cassette mutation), genetic homologous recombination, primer extension method and PCR, or any optional combinations thereof. The above amino acid sequence comprising one or few amino acids that are substituted, deleted, inserted or added have homology (identity) of 90% or more, preferably 95% or more, more preferably 99% or more with a full-length amino acid sequence in the original amino acid sequence.

Various structures comprised in the humanized highly functional bispecific antibody (BsAb) are disclosed in Patent Document 2.

The first type of the present LH-type BsAb (i) (LH-type Ex3 scDb) has a structure represented by (5L OH)-(a peptide linker)-(OL5H) or (OL5H)-(a peptide linker)-(5LOH). Thus, the two kinds of the polypeptide chains constituting the LH-type Ex3, 5LOH and OL5H, are further linked together by the peptide linker to form a single polypeptide chain as a whole. As a result, the structure of this LH-type BsAb molecule has been more stabilized than Ex3. Furthermore, said BsAb may be produced by a single kind of an expression vector, so that more homogeneous BsAb molecule may be prepared than LH-type Ex3. The term "scDb" means a single-chain diabody-type bispecific antibody.

Any linker known in the art or one modified therefrom may be optionally selected and used as the peptide linker in the present invention without any limitation in its length as long as it can assemble OH and OL, or 5H and 5L together to form an antigen-binding site that can specifically react with each antigen. The above peptide linker may be inserted between 5H and 5L, or between OH and OL.

The second type of the present BsAb (ii) (LH-type Ex3-Fc) has the structure wherein the humanized diabody-type bispecific antibody (LH-type Ex3) consisting of the two kinds of the single-chain polypeptides of (5LOH) and (OL5H) is bonded to the two Fc regions of the human antibody via each hinge region through either of the two single-chain polypeptides. Thus, this BsAb is composed of one of the two kinds of the single-chain polypeptide constituting LH-type Ex3, which has been bonded to the Fc region of the human antibody via each hinge region (for example, (OL5H)-(hinge region)-Fc region), and the other polypeptide (for example, 5LOH). The above antibody may be produced by expressing the two kinds of the single-chain polypeptides and assembling them. The term "Fc region" means two domains (CH2 and CH3) located at C-end of the heavy chain constituting a constant region (C region).

The third type of the present BsAb (iii) (LH-type Ex3 scDb-Fc) has the structure wherein the single-chain polypeptide of the first type of the present BsAb (i) (LH-type Ex3 scDb) is bonded to the two Fc regions of the human antibody via each hinge region in the second type of the present BsAb (ii) instead of LH-type Ex3. The single-chain polypeptide of (5LOH)-(a peptide linker)-(OL5H) or (OL5H)-(a peptide linker)-(5LOH) may be bonded with the hinge region through any one of the two kinds of the heavy and light chain variable regions in the above single-chain polypeptides.

As the number of the domains constituting the second and third type of the present LH-type BsAb of the types (ii) and (iii) is the same as that of an immunoglobulin molecule, it is considered that these LH-type BsAb have a space structure similar to that of the immunoglobulin molecule. A protease cleavage site may be inserted between the hinge region and LH-type Ex3 or LH-type Ex3 scDb in the second or third type of the present LH-type BsAb. As a result, LH-type Ex3 or LH-type Ex3 scDb can be easily produced by digesting these LH-type BsAb with the protease followed by the purification steps mentioned below. The LH-type Ex3 or LH-type Ex3 scDb thus produced by the protease digestion will show stronger cytotoxicity than those produced by the conventional methods.

As any one of the present LH-type BsAb of the types (ii) and (iii) comprises the human Fc region, it may be easily purified with Protein A. They will further induce an antibody-dependent cellular cytotoxicity (ADCC) and cell-dependent cytokine (CDC). They also show an advantage that they can bind divalently to each antigen, which is not found with LH-type Ex3. The peptide linker comprised in the present LH-type BsAb may have about 1-20 amino acids, preferably about 1-15 amino acids, more preferably about 2-10 amino acids.

There is no limitation on the constant region or Fc region comprised in the present LH-type BsAb as long as it is derived from the human antibody. For example, CL may be derived from κ or λ, chain. Fc region or the heavy chain constant region is usually derived from γ chain of IgG. The amino acid sequences represented by SEQ ID NOS: 29, 30 and 33 disclosed in Patent Document 2 are representative examples of CH1, CH2 & CH3, and CL, respectively.

Figure 3:
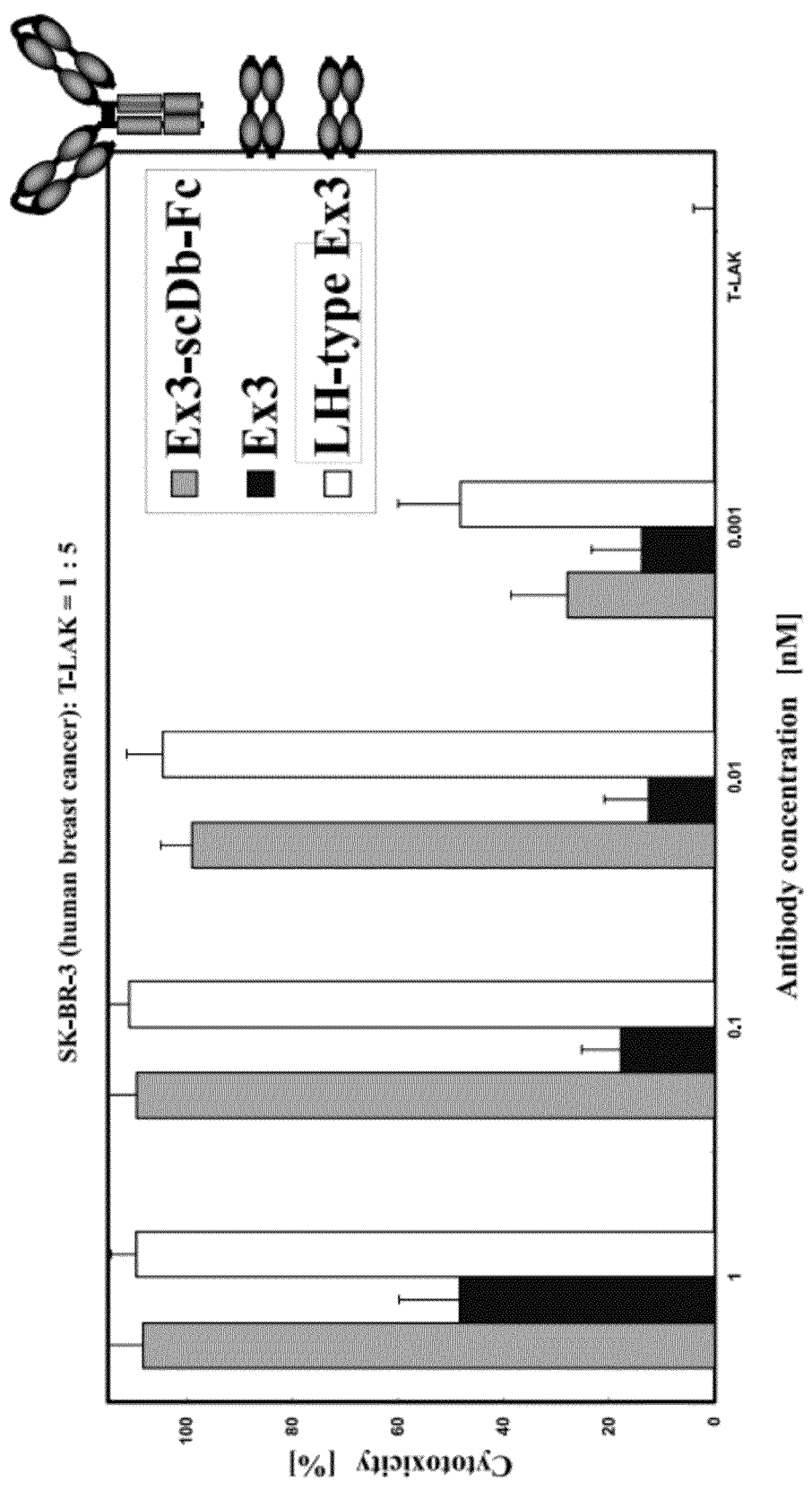
FIG. 3 shows the results of Cytotoxicity Test (cell-growth inhibition test) on human breast cancer cell, SK-BR-3 (ATCC No. HTB-30) with the LH-diabody type bispecific antibody, the humanized Ex3 disclosed in Patent Document 1 and Ex3-scDb-Fc disclosed in Patent Document 2.
Figure 4:
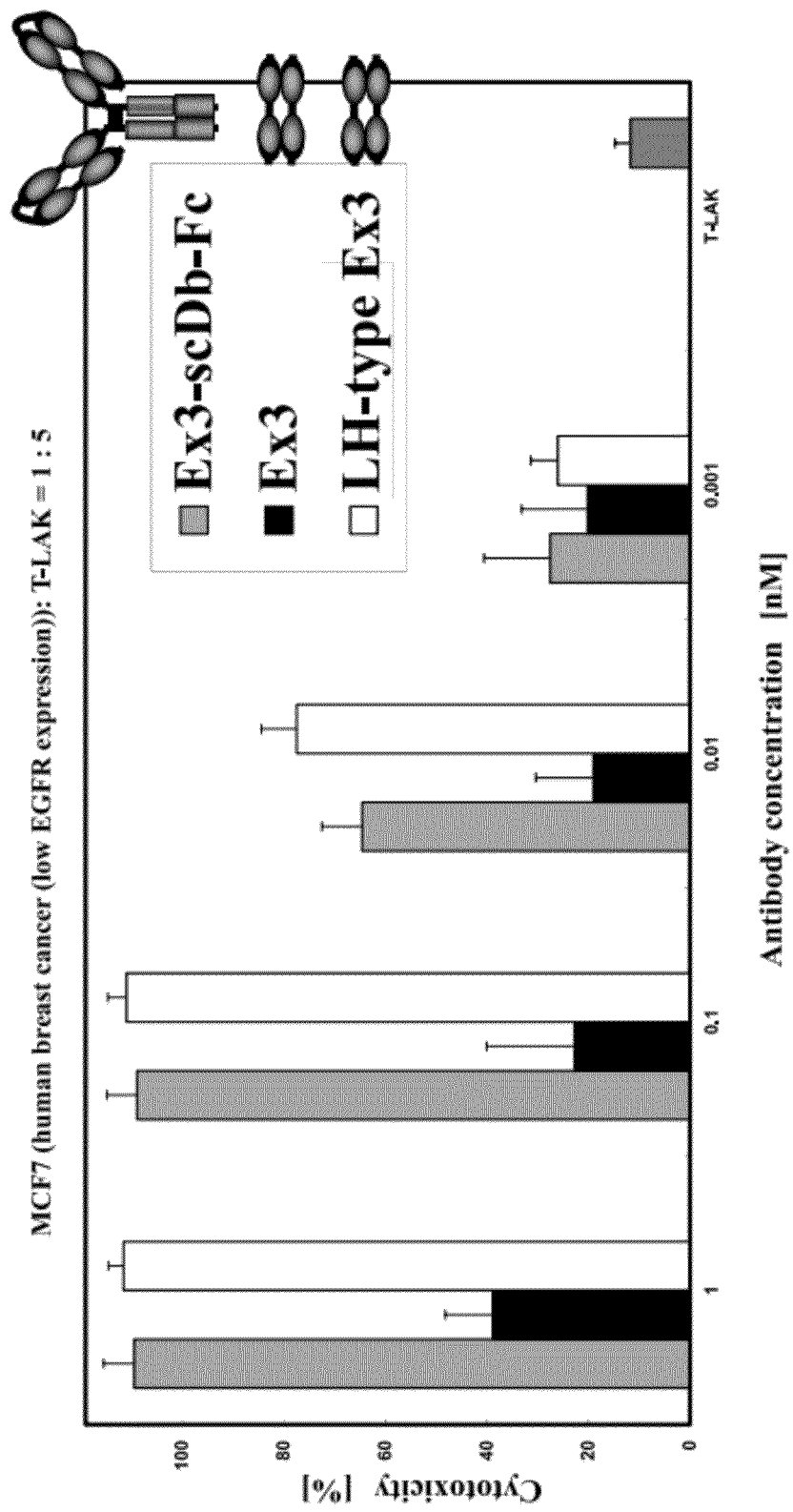
FIG. 4 shows the results of Cytotoxicity Test (cell-growth inhibition test) on human breast cancer cell (low EGFR-expressing type), MCF7 (ATCC No. HTB-22) with the LH-diabody type bispecific antibody, the humanized Ex3 disclosed in Patent Document 1 and Ex3-scDb-Fc disclosed in Patent Document 2.
Figure 5:
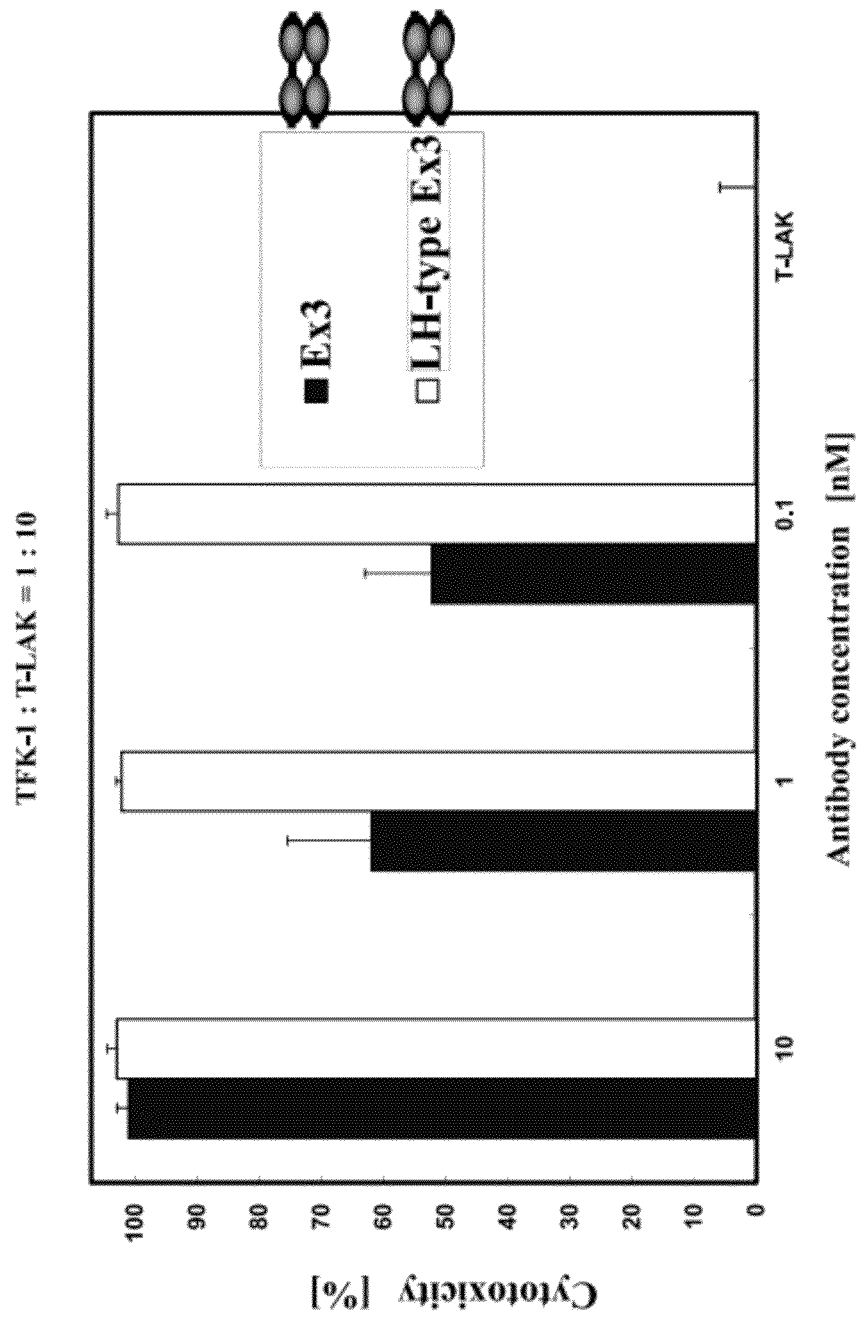
FIG. 5 shows the results of Cytotoxicity Test (cell-growth inhibition test) on human gallbladder cancer cell, TFK-1 (Cell Resource Center for Biomedical Research, Institute of Development, Aging and Cancer, TOHOKU University, ID:TKG036) with the LH-diabody type bispecific antibody, the humanized Ex3 disclosed in Patent Document 1.
Figure 6:
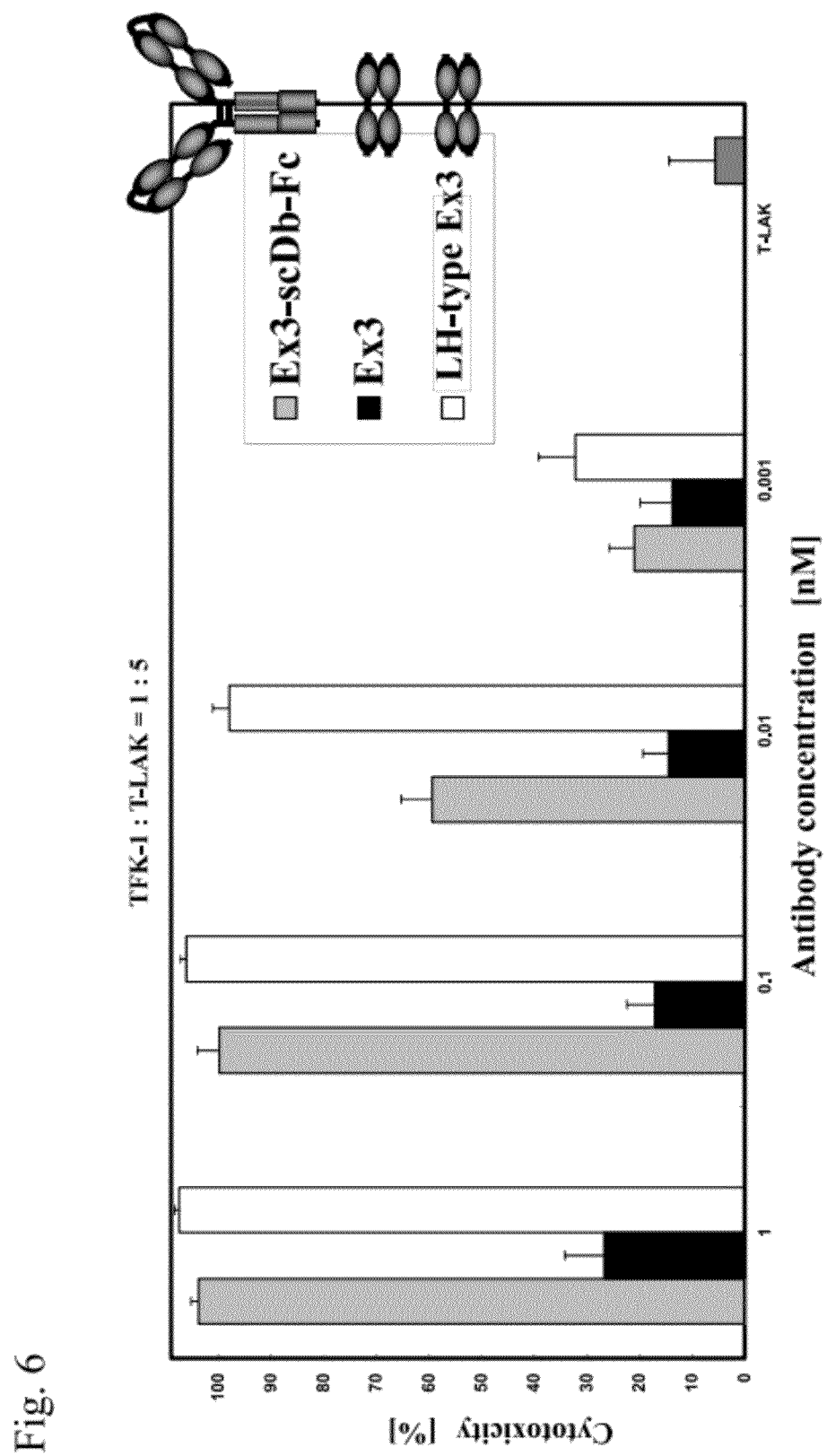
FIG. 6 shows the results of Cytotoxicity Test (cell-growth inhibition test) on human gallbladder cancer cell, TFK-1 (Cell Resource Center for Biomedical Research, Institute of Development, Aging and Cancer, TOHOKU University, ID:TKG036) with the LH-diabody type bispecific antibody, the humanized Ex3 disclosed in Patent Document 1 and Ex3-scDb-Fc disclosed in Patent Document 2.

Representative examples of the amino acid sequences of the PreSission sequence, hinge region, peptide linker, signal peptide, etc. that are comprised in the single-chain polypeptides constituting the present LH-type BsAb are shown in FIGS. 3-3 and 3-4 of Patent Document 2. The PreSission sequence comprises a protease-cleavage site. There is no limitation on the kind of protease used in the present invention, and any enzyme known in the art such as Thrombin and Factor Xa may be used, and the amino acid sequence comprising the protease-cleavage site may be optionally selected.

The representative examples of the nucleic acid molecules (oligonucleotides) encoding the whole or part of the amino acid sequences of the single-chain polypeptide according to the present invention have the nucleotide sequences shown in the above SEQ ID NOS. Furthermore, as a nucleic acid molecule with the nucleotide sequence having homology of 90% or more, preferably 95% or more, more preferably 99% or more with a full-length nucleotide sequence represented by the same SEQ ID NOS are considered to encode a polypeptide having substantially the same property and function as that of the original polypeptide or part thereof, the above nucleic acid molecule is included in the nucleic acid molecule of the present invention. Although the nucleic acid molecule comprises a nucleotide sequence encoding at least either of the two kinds of the single-chain polypeptides constituting LH-diabody type BsAb according to the present invention, it preferably comprises two kinds of nucleotide sequences together, each of which encodes one of the two kinds of said single-chain polypeptides, respectively.

In order to determine the homology between two amino acid or nucleotide sequences, they may be preliminarily treated into an optimum condition for comparison. For example, a gap may be inserted into one of the sequences to optimize the alignment with the other sequence, followed by the comparison of amino acid or nucleotide at each site. When the same amino acid or nucleotide exists at a corresponding site of the first and second sequences, these two sequences are considered to be identical with respect to said site. Homology between two sequences is shown by a percent ratio of the number of the identical sites over the total number of amino acids or nucleotides between the two sequences.

The term "homology" in this specification means an amount (or a number) of the amino acids in an amino acid sequence or the nucleotides in a nucleotide sequence, which are determined to be identical with each other in the relationship between two sequences, showing an extent of the correlation between the two polypeptide or nucleotide sequences. The homology may be easily calculated. The term "homology" or "identity" is well known in the art, and many methods for the calculation of such homology are known, among them. For example, Lesk, A. M. (Ed.), Computational Molecular Biology, Oxford University Press, New York, (1988); Smith, D. W. (Ed.), Biocomputing: Informatics and Genome Projects, Academic Press, New York, (1993); Grifin, A. M. & Grifin, H. G (Ed.), Computer Analysis of Sequence Data: Part I, Human Press, New Jersey, (1994); von Heinje, G., Sequence Analysis in Molecular Biology, Academic Press, New York, (1987); Gribskov, M. & Devereux, J. (Ed.), Sequence Analysis Primer, M-Stockton Press, New York, (1991). A general method for the determination of the homology between two sequences is disclosed, for example, in Martin, J. Bishop (Ed.), Guide to Huge Computers, Academic Press, San Diego, (1994); Carillo, H. & Lipman, D., SIAM J. Applied Math., 48: 1073 (1988). A preferable method for the determination of the homology between two sequences is, for example, one designed to obtain a largely related part between said two sequences. Some of them are provided as a computer program. Preferable examples of the computer programs for the determination of the homology between two sequences include GCG program package (Devereux, J. et al., Nucleic Acids Research, 12(1): 387 (1984)), BLASTP, BLASTN, FASTA (Atschul, S. F. et al., J. Molec. Biol., 215: 403 (1990).

The nucleic acid of the present invention further includes a DNA molecule that hybridizes with a DNA comprising a nucleotide sequence complementary to the nucleotide sequence represented by the above SEQ ID NOS under stringent conditions, and encodes a polypeptide having substantially the same property and function as that of the polypeptides represented by the above SEQ ID NOS.

Hybridization may be carried out by or in accordance with a method well known in the art such as that described in Molecular cloning third. ed. (Cold Spring Harbor Lab. Press, 2001). Hybridization may be done in accordance with an instruction or manual attached to a commercially available library.

Hybridization may be carried out by or in accordance with a method well known in the art such as that described in Current protocols in molecular Biology edited by Frederick M. Ausbel et al., 1987). Hybridization may be done in accordance with an instruction or manual attached to a commercially available library.

The phrase "stringent conditions" in this specification may be defined by a suitable combination of salt concentration, organic solvent (for example, formamide), temperature, and other known conditions. Thus, stringency will be increased by the decrease of salt concentration, or the increase of an organic solvent concentration or hybridization temperature. The washing conditions after the hybridization may also affect the stringency. The washing conditions are also defined by salt concentration and temperature. The stringency of washing will be increased by the decrease of salt concentration or the increase of temperature.

Accordingly, the "stringent conditions" in this specification means conditions under which a specific hybrid can be formed only between the nucleotide sequences having homology of about 80% or more, preferably about 90% or more, more preferably about 99% or more on a total average. Specifically, they may be sodium concentration of 150-900 mM, preferably 600-900 mM, pH6-8 at 60-68° C. One example of the stringent conditions is hybridization in 5×SSC (750 mM NaCl, 75 mM $Na_3$ Citrate), 1% SDS, 5× Denhart solution 50% formaldehyde at 42° C., followed by the washing with 0.1×SSC (15 mM NaCl, 1.5 mM $Na_3$ Citrate), 0.1% SDS at 55° C.

Furthermore, the nucleic acid encoding the humanized variable regions in the single-chain polypeptide of the present invention may be synthesized by means of an over-lapping PCR method based on a pre-determined amino acid sequence. The nucleic acid used herein has no limitation in its chemical structure or preparation route, as long as it is a molecule encoding the single-chain polypeptide, including gDNA, cDNA chemically-synthesized DNA and mRNA.

Specifically, the nucleic acid according to the present invention may be isolated from cDNA library by means of hybridization or PCR based on the sequences disclosed in literatures. The thus isolated DNA may be inserted in an expression vector, with which a host cell such E. coli, COS cell, CHO cell or myeloma not expressing immunoglobulin are transfected to synthesize a monoclonal antibody in the thus transformed host cells. PCR may be carried out in accordance with a method known in the art, or substantially the same or altered methods. The methods disclosed in, for example, R. Saiki, et al., Science, 230:1350, 1985; R. Saiki, et al., Science, 239:487, 1988; H. A. Erlich ed., PCR Technology, Stockton Press, 1989; D. M. Glover et al., ed., "DNA Cloning," $2^{nd}$. ed., Vol. 1, (The Practical Approach Series), IRL Press, Oxford University Press (1995); M. A. Innis et al., ed., "PCR Protocols: a guide to methods and applications," Academic Press, New York (1990); M. J. McPherson, P. Quirke and GR. Taylor (Ed.), PCR: a practical approach, IRL Press, Oxford (1991); M. A. Frohman et al., Proc. Natl. Acad. Sci. USA, 85, 8998-9002 (1988), and their modified and altered methods may be used in the present invention. PCR may be performed with use of a commercially available kit in accordance with manufacturer's protocols.

The sequencing method of nucleic acids such as DNA may be referred to Sanger et al., Proc. Natl. Acad. Sci. USA 74:5463-5467 (1977). A general method for recombinant DNA techniques may be referred to J. Sambrook, E. F. Fritsch & T. Maniatis (ed.), "Molecular Cloning: A Laboratory Manual ($2^{nd}$ edition)", Cold Spring Harbor Laboratory Press, Cold Spring Harbor, N.Y. (1989) and D. M. Glover et al. (ed.), $2^{nd}$ ed., Vol. 1 to 4 (The Practical Approach Series), IRL Press, Oxford University Press (1995).

The nucleic acid encoding the single-chain polypeptide constituting the present LH-type BsAb or each region contained therein may be modified or altered so that it will optionally encode a desired peptide or amino acid depending on the purpose. The techniques for such modification or alternation are disclosed in Mutagenesis: a Practical Approach, M. J. McPherson (ed.), IRL Press, Oxford, UK (1991), including a site-specific mutagenesis introduction method, cassette mutagenesis induction method and PCR mutagenesis method.

The term "modification (or alternation)" as used herein refers to insertion, deletion or substitution of base(s) in at least one codon encoding an amino acid residue in the originally obtained nucleic acid. It includes alternation of the amino acid sequence per se of the single-chain polypeptide by replacing a codon encoding the original amino acid with a codon encoding another amino acid.

Alternatively, the nucleic acid encoding the single-chain polypeptide may be altered without changing the amino acid per se, by using a codon suitable for a host cell (an optimum codon). With the use of the optimum codon, expression efficiency of the single-chain polypeptide in the host cell will be improved.

The LH-type BsAb according to the present invention may be produced by various methods well known in the art such as genetic engineering technique and chemical synthesis. For example, the genetic engineering technique includes producing a replicable cloning vector or an expression vector containing the nucleic acid molecule encoding each of the two kinds of the single-chain polypeptides constituting the above bispecific antibody, transforming a host cell with the vector, culturing the transformed host cell to express each of the single-chain polypeptides, collecting and purifying said single-chain polypeptides, assembling the two kinds of the single-chain polypeptides, and separating and collecting the bispecific antibody thus formed.

The term "replicable expression vector" or "expression vector" as used herein refers to a piece of DNA (usually double-stranded) that may comprise a fragment of a foreign DNA fragment inserted therein. The foreign DNA is also defined as a "heterologous DNA", which cannot be found naturally in a host cell in interest. The vector is used to carry or convey the foreign or heterologous DNA into an appropriate host cell. Once the vector is introduced into the host cell, it may be replicated independently from a chromosomal DNA of the host cell to produce copies of the vector and foreign DNA inserted therein. The vector also comprises elements essential for translating the foreign DNA into a polypeptide so that the polypeptide molecules encoded by the foreign DNA will be synthesized very quickly.

The above vector means a DNA construct comprising an appropriate control sequence and DNA sequence that are operably linked together (i.e., linked together so that the foreign DNA can be expressed). The control sequence includes a promoter for transcription, an optional operator sequence to regulate the transcription, a sequence encoding an appropriate mRNA ribosome-biding site, an enhancer, a polyadenylation sequence, and a sequence controlling the termination of transcription and translation. The vector may further comprise various sequences known in the art, such as a restriction enzyme cleaving site, a marker gene (selection gene) such as a drug-resistant gene, a signal sequence, and a leader sequence. These sequences and elements may be optionally selected by those skilled in the art depending on the kinds of the foreign DNA and host cell, and conditions of culture medium. Furthermore, various peptide tags (c-myc and His-tag, for example) known in the art may be contained at its end, etc.

The vector may be in any form such as a plasmid, phage particle, or just simply genomic insert. Once the appropriate host cell is transformed with the vector, the vector will be replicated or function independently from the genome of the host cell, or the vector will alternatively be integrated into the genome of the cell.

Any cell known in the art may be used as the host cell, for example, there may be mentioned prokaryotic cells such as including E. coli, eukaryotic cells such as mammalian cells such Chinese hamster ovary (CHO) cell and human cells, yeast, and insect cells. For example, BL21 star (DE3) strain is cultured in 2×YT culture medium at about 28° C. and induced with IPTG of about 0.5 mM, so that the yield of the present LK-type bispecific antibody may be highly improved so as to increase its production efficiency.

Although the single-chain polypeptide obtained by the expression in the host cell is usually secreted and collected from the culture medium, it may be also collected from cell lysate when it is directly expressed without a secretion signal. In case the single-chain polypeptide has a membrane-binding property, it may be released from the membrane with an appropriate surfactant such as Triton-X100.

Purification of the polypeptide may be carried out by any method known to those skilled in the art such as centrifugation, hydroxyapatite chromatography, gel electrophoresis, dialysis, separation on ion-exchange chromatography, ethanol precipitation, reverse phase HPLC, silica chromatography, heparin-sepharose chromatography, anion- or cation-resin chromatography such as polyaspartic acid column, chromato-focusing, SDS-PAGE, precipitation with ammonium sulfate, and affinity chromatography. The affinity chromatography, which utilizes affinity with a peptide tag of the single-chain polypeptide, is one of the preferred purification techniques with a high efficiency.

Since the collected single-chain polypeptide may be often included in an insoluble fraction, the polypeptide is preferably purified after being solubilized and denatured. The solubilization treatment may be carried out with the use of any agent known in the art, including alcohol such ethanol, a dissolving agent such as guanidine hydrochloride and urea. The present LH-type BsAb is produced by assembling or rewinding the two kinds of the single-chain polypeptides thus purified, and separating and collecting the thus formed antibody molecule.

Assembling treatment will bring a single-chain polypeptide back in its appropriate spatial arrangement in which a desired biological activity is shown. Since this treatment may also bring polypeptides or domains back into their assembling state, it may be considered "re-assembling." It may be also called "re-constitution" or "refolding" in view of gaining the desired biological activity. The assembling treatment may be carried out by any method known in the art, preferably by gradually lowering the concentration of a denaturing agent such as guanidine hydrochloride in a solution comprising the single-chain polypeptide by means of dialysis. During these processes, an anti-coagulant or oxidizing agent may be optionally added in a reaction system in order to promote the oxidation. The separation and collection of the present highly functional BsAb thus formed may be done by any method known in the art as well.

As already described above, the LH-type BsAb according to the present invention may be prepared from the supernatant of a culture medium, periplasm fraction, intracellular soluble fraction and intracellular insoluble fraction.

It is possible to transform a host cell with the co-expression vector containing a nucleic acid molecule encoding both of the two kinds of the single-chain polypeptides constituting the LH-type bispecific antibody of the present invention, or with the two kinds of an expression vector containing a nucleic acid molecule encoding each of the two kinds of said single-chain polypeptides, respectively, culturing the transformed host cell so as to express the two kinds of the single-chain polypeptides, allowing the transformed cell to form the LH-type bispecific antibody in said cell, and separating and collecting it from supernatant of the culture medium or intracellular soluble fraction.

In such case, the above assembling or rewinding treatment is unnecessary so that a high productivity can be achieved at a low cost.

Furthermore, it is preferable to culture BL21 star (DE3) strain (Invitrogen) as a host cell in 2×YT culture medium with shaking at 28° C. overnight, to induce with IPTG at a final concentration of 0.5 mM when O.D at 600 nm becomes about 5, and to collect the desired protein 16 hours later of the induction from the supernatant of the culture medium and periplasm fraction after an osmotic pressure treatment.

A pharmaceutical preparation according to the present invention comprises an active ingredient selected from the group consisting of the present LH-type BsAb, the single-chain polypeptide, the nucleic acid, the vector, and the host cell described in the above. As shown by the examples in the present specification, since the active ingredient has an activity of eliminating, hurting, damaging and/or reducing tumor cells expressing EGFR in vitro and in vivo, the present pharmaceutical preparation is used as an anti-tumor agent.

An effective amount of the active ingredient may be optionally determined by those skilled in the art depending on the purpose of treatment, medical conditions of a patient to be treated such as kind, site or size of tumor, and administration route. A typical dose or daily dose may be first determined in vitro by using an assay method of growth or existence of the tumors known in the art, then determined with use of such an appropriate animal model as to allow extrapolation of the resulting dose range to human patients.

The pharmaceutical preparation of the present invention may optionally comprise various kinds of pharmaceutically acceptable components known in the art such as carrier, excipient, buffer, stabilizing agent and the like, depending on various factors such as the kind of the active ingredients, its formulation form, the route and purpose of administration, medical conditions of patient.

The pharmaceutical preparation of the present invention may be formulated into any form such as pill, liquid, powder, gel, air spray, microcapsule, and colloidal dispersion (liposome, micro emulsion, etc.).

The pharmaceutical preparation may be administered by injecting or infusing intravenously, intraperitoneally, intracerebrally, intraspinally, intramuscularly, intraocularly, intraarterially, especially intrabiriarily, or via diseased tissue, or with use of a constant releasing agent system. The active ingredient according to the present invention may be administered through continuous fluid infusion or massive injection. The pharmaceutical preparation according to the present invention is preferably administered in combination with the cell having phagocytosis or cytotoxic activity. Alternatively, the active ingredient such as the present BsAb may be mixed with the above cells so as to bind to them before its administration.

The constant releasing agent generally refers to a formulation that can release the active ingredient of the present invention for a certain period of time. One of the preferred constant releasing agents comprises a semi-permeable carrier of solid hydrophobic polymer such as protein, which is shaped into a form such as film or micro capsule.

The pharmaceutical preparation according to the present invention may be produced by a method that is optionally selected from, for example, "Guide Book of Japanese Pharmacopoeia", Ed. of Editorial Committee of Japanese Pharmacopoeia, Version No. 13, published Jul. 10, 1996 by Hirokawa publishing company The terms as used in the present specification and drawings are based on IUPAC-IUB Commission on Biochemical Nomenclature or on meanings of the terms conventionally used in the art.

The present invention will be explained more in detail by referring to the Examples, which are provided only for describing the specific embodiments of the present invention, but not for limiting the scope of the present invention. It is therefore to be understood that various embodiments based on the inventive concept of the present specification may be practiced within the scope of the present invention.

The following examples were or can be carried out with standard techniques well known to those skilled in the art unless otherwise described. Thus, unless otherwise described, specific procedures and treating conditions are in accordance with J. Sambrook, E. F. Fritsch & T. Maniatis, "Molecular Cloning", 2nd ed., Cold Spring Harbor Laboratory, Cold Spring Harbor, N.Y. (1989) and D. M. Glover et al. ed., "DNA Cloning", 2nd ed., Vol. 1 to 4, (The Practical Approach Series), IRL Press, Oxford University Press (1995) (DNA cloning), and with H. A. Erlich ed., PCR Technology, Stockton Press, 1989; D. M. Glover et al. ed., "DNA Cloning", 2nd ed., Vol. 1, (The Practical Approach Series), IRL Press, Oxford University Press (1995) and M. A. Innis et al. ed., "PCR Protocols", Academic Press, New York (1990) (PCR). A commercially available agent and kit were used in accordance with protocols attached thereto.

EXAMPLE 1

Production of the LH-Diabody Type Bispecific Antibody

The LH-diabody type bispecific antibody according to the present invention was prepared in the following manner.

An expression vector was constructed as follows based on the expression vector fir the humanized diabody-type bispecific antibody for EGFR and CD3 (Patent Document 1 and Patent Document 2, Reference Examples 1-4).

Thus, the humanized 5L ("h5L") and humanized OH ("hOH") were amplified with PCR using A-B primers and C-D primers, respectively. The resulting PCR products were then mixed and PCR-amplified using A-D primers. The resulting PCR product was digested with NcoI and SacII and inserted into pRA vector to give a vector pRA-h5LhOH for the expression of h5LhOH comprising a linker sequence of SGGGG, which is one of the hetero scFvs constituting a LH-type diabody. Similarly, the humanized OL ("hOL") and humanized 5H ("h5H") were amplified with PCR using E-F primers and G-H primers, respectively. The resulting PCR products were then mixed and PCR-amplified using E-H primers. The resulting PCR product was digested with NcoI and SacII and inserted into pRA vector to give a vector pRA-hOLh5H for the expression of hOLh5H comprising a linker sequence of SGGGG, which is the other of the hetero scFvs constituting the LH-type diabody. Further, h5LhOH was PCR-amplified using I-J primers. The resulting PCR product was digested with SpeI and BamHI and inserted into the backward of hOLh5H in the vector pRA-hOLh5H to give a co-expression vector for the production of the LH-diabody type bispecific antibody according to the present invention.

```
A: NcoI-5L:     5'-NNNNCCATGGCCGATATTGTGATGACCCAGAGCCCG-3':      [SEQ ID NO: 9]

B: 5LSG4:       5'-CTGGCCACCGCCACCAGATTTAATTTCCACTTTGGTGCCACCGCC-3' [SEQ ID NO: 10]

C: SG4OH:       5'-AAATCTGGTGGCGGTGGCCAGGTGCAACTGGTGCAGAGCGGC-3'  [SEQ ID NO: 11]

D: OH-SacII:    5'-NNNNAGCCGCGGAGCTAACGGTCACCGGGGTGCCCTGGCC-3'    [SEQ ID NO: 12]

E: NcoI-OL:     5'-NNNNCCATGGCCGATATTCAGATGACCCAGAGCCCG-3'        [SEQ ID NO: 13]

F: OLSG4:       5'-CTGGCCACCGCCACCAGAGGTAATCTGCAGTTTGGTACCCTG-3'  [SEQ ID NO: 14]

G: SG45H:       5'-ACCTCTGGTGGCGGTGGCCAGGTGCAACTGGTTCAGAGCGGC-3'  [SEQ ID NO: 15]

H: 5H-Sac II:   5'-NNNNAGCCGCGGAGCTCACGGTAACCAGCGTACC-3'          [SEQ ID NO: 16]

I: SpeI-pel-B:  5'-ACTAGTTATTTCAAGGAGACAGTCATAATG-3'              [SEQ ID NO: 17]

J: His-BamHI:   5'-CACCATCATCACCACCATTAATAGCGGATTC-3'             [SEQ ID NO: 18]
```

A c-myc peptide tag for detection and a His-tag (His×6: histidine-hexamer) for purification were introduced successively at C-end of the vector. According to the conventional method, E. coli. was transformed with the above co-expression vector, cultured in 2×YT culture medium at 28° C. overnight and induced with IPTG of 0.5 mM. The LH-type BsAb according to the present invention was then prepared from the supernatant of the culture medium, periplasm fraction, intracellular soluble fraction and intracellular insoluble fraction (FIG. 1). The resulting LH-type BsAb is represented as "LH-type Ex3" in the figures.

The humanized variable region of the light chain (5L) and the humanized variable region of the heavy chain (5H) of the anti-human EGF receptor 1 antibody 528, and the humanized variable region of the light chain (OL) and the humanized variable region of the heavy chain (OH) of the anti-CD3 antibody OKT, which are comprised in the single-chain polypeptides that constitute the above LH-diabody type humanized bispecific antibody of the present invention have a nucleotide sequence and an amino acid sequence represented by SEQ ID NOS: 1 and 2, 3 and 4, 5 and 6, and, 7 and 8, respectively.

EXAMPLE 2

Production of the LH-Type Highly Functional Bispecific Antibody

An Expression vector (Ex3 scDb-Fc) for the production of the LH-type highly functional bispecific antibody (LH-type Ex3 scDb) was constructed in accordance with the methods described in Example 1 of Patent Document 2 (the first to third types) using appropriate primers designed based on the above sequences. The scDb-Fc was then prepared using CHO cell as a host cell in accordance with Example 2 of Patent Document 2. However, the OL5H was inserted into the upstream of 5LOH via the peptide linker in order to first construct the Ex3 scDb having the structure of (OL5H)-(a peptide linker)-(5LOH) as the first type of the LH-type Ex3 scDb. The LH-type Ex3 scDb-Fc was then prepared based on the LH-type Ex3 scDb. As a result, an antibody production yield of about 1 mg per 1L of culture medium was obtained after its purification.

EXAMPLE 3

Cytotoxicity Test (MTS Assay) of the LH-Diabody Type Bispecific Antibody and LH-Type Highly Functional Bispecific Antibody MTS assay was done using the LH_of the LH-diabody type bispecific antibody prepared in Example 1 and the LH-type highly functional bispecific antibody prepared in Example 2 as follows.

Figure 7:
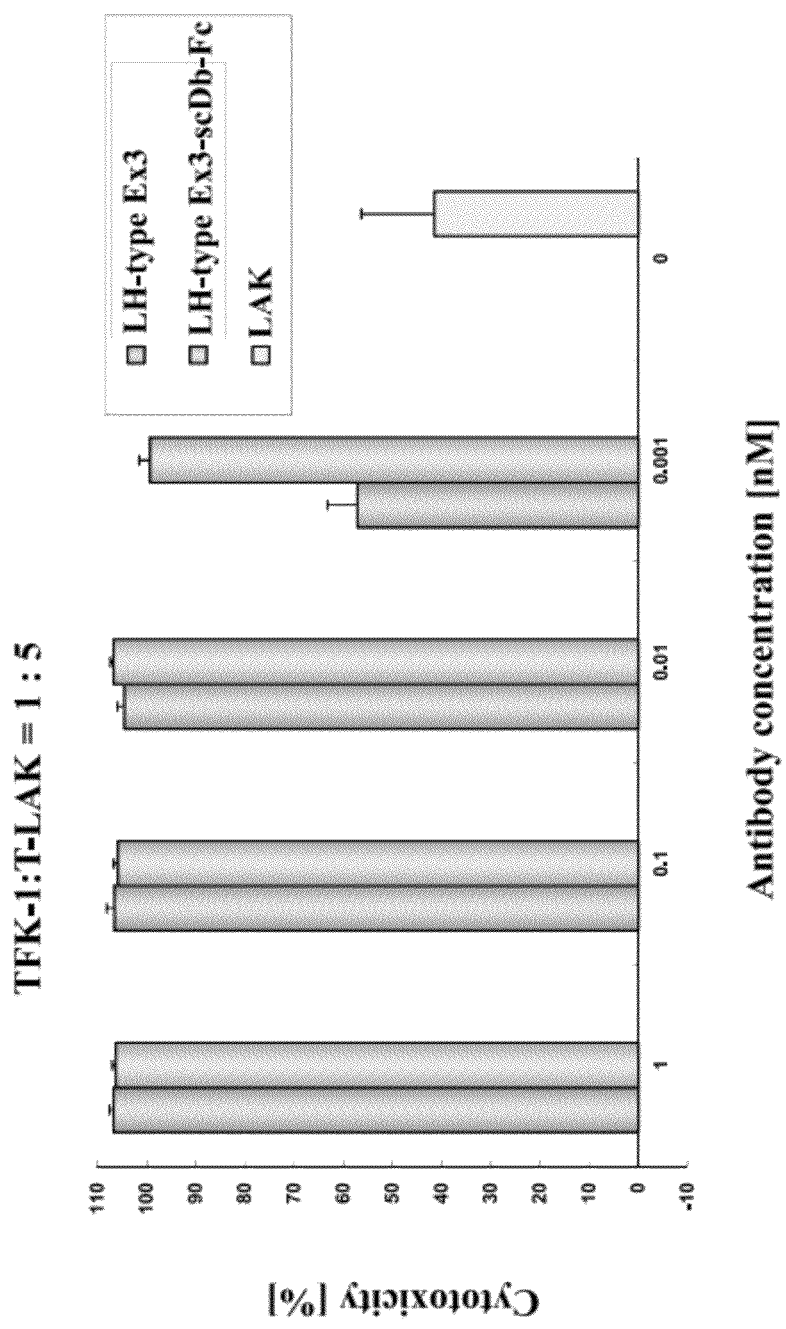
FIG. 7 shows the results of Cytotoxicity Test (cell-growth inhibition test) on human gallbladder cancer cell, TFK-1 (Cell Resource Center for Biomedical Research, Institute of Development, Aging and Cancer, TOHOKU University, ID:TKG036) with the LH-diabody type bispecific antibody (LH-type Ex3) and the humanized highly functional bispecific antibody (LH-type Ex3 scDb-Fc). In this figure, the left bars show LH-type Ex3 and the right bars show LH-type Ex3 scDb-Fc in each antibody concentration.

MTS assay was done to determine the degree of damage in human epidermoid cancer cell, A431 (ATCC No. CRL-1555), human breast cancer cell, SK-BR-3 (ATCC No. HTB-30), human breast cancer cell (low EGFR-expressing type), MCF7 (ATCC No. HTB-22), and TFK-1 (Cell Resource Center for Biomedical Research, Institute of Development, Aging and Cancer, TOHOKU University, ID:TKG036) with the LH diabody-type bispecific antibody, and compared those with the humanized Ex3 (described just as "Ex3" in Figures) of Patent Document 1 and Ex3-scDb-Fc of Patent Document 2. Each cell sample was adjusted by counting to contain $5 \times 10^3$ cells per 100 µL of RPMI 1640 (10% FBS), and its aliquot of 100 µL was dispensed into each well of a 96-well plate to stand still overnight at 37° C. After being diluted with RPMI to a desired concentration of the antibody according to the present invention, 50 µL of which was put into each well of the above plate. T-LAK cell was diluted with RPMI to a desired E/T (Effector (T-LAK cell)/Target (TFK-1 cell)) ratio, and 50 µL of the cell solution was put into each well of the above plate as well. After being cultured for 48 hours at 37° C., the culture medium was removed. The cells were then washed with PBS, mixed with MTS (CellTiter 96 AQueous Non-Radioactive Cell Proliferation Assay, Promega Co.), PMS (CellTiter 96 AQueous Non-Radioactive Cell Proliferation Assay, Promega Co.), and RPMI, and incubated for 30-60 min. at 37° C., followed by the detection of absorbance at 490 nm with a plate reader. It was confirmed that the LH-diabody type bispecific antibody showed a higher cytotoxicity by about one order than that of the humanized Ex3, and a similar cytotoxicity to that of the IgG-like highly functional bispecific antibody Ex3-scDb-Fc on any one of the cells, as shown in FIG. 2-FIG. 6. Furthermore, the cytotoxicity on TFK-1 was compared between the LH-type Ex3 and the LH-type Ex3 scDb-Fc, demonstrating that the LH-type Ex3 scDb-Fc showed much more significant cytotoxicity than the LH-type Ex3 (FIG. 7).

INDUSTRIAL APPLICABILITY

A high cost of the production of an antibody drug has recently become a serious problem. As a result, it has been a worldwide trend to produce a low molecular-weight antibody that can be produced economically in E. coli. On the other hand, although more than ten years have already passed since the low molecular-weight antibody was developed for cancer therapy, it has hardly progressed into a clinical test due to problems in its production and actual therapeutic effects. However, it seems that the antibody drug has the potential as a drug if its production cost or function is improved.

It is expected that the LH-type bispecific antibody and the method for its production provided by the present invention will increase the clinical application of the diabody-type bispecific antibody, and accelerate the development and seed-search of such molecules by pharmaceutical companies.

---

What is claimed is:

1. A single-chain polypeptide which is either a first or a second polypeptide of a diabody-type bispecific antibody, said diabody-type bispecific antibody consisting of said first polypeptide comprising a humanized variable region of the light chain (5L) of an anti-human EGF receptor 1 antibody 528 and a humanized variable region of the heavy chain (OH) of an anti-CD3 antibody OKT in this order from its N-end to C-end and said second polypeptide comprising a humanized variable region of the light chain (OL) of an anti-CD3 antibody OKT and a humanized variable region of the heavy chain (5H) of an anti-human EGF receptor 1 antibody 528 in this order from its N-end to C-end.

2. A single-chain polypeptide which has the structure of (5LOH) or (OL5H) bonded to Fc region of a human antibody via hinge region of a humanized highly functional bispecific antibody comprising humanized variable regions of the heavy chain (5H) and the light chain (5L) of an anti-human EGF receptor 1 antibody 528, and humanized variable regions of the heavy chain (OH) and the light chain (OL) of an anti-CD3 antibody OKT3 having the following structure: a humanized diabody-type bispecific antibody consisting of two kinds of the single-chain polypeptides of (5LOH) and (OL5H) is bonded to two Fc regions of a human antibody via each hinge region through either of the two single-chain polypeptides.

3. A diabody-type bispecific antibody consisting of a first polypeptide comprising a humanized variable region of the light chain (5L) of an anti-human EGF receptor 1 antibody 528 and a humanized variable region of the heavy chain (OH) of an anti-CD3 antibody OKT in this order from its N-end to C-end; and a second polypeptide comprising a humanized variable region of the light chain (OL) of an anti-CD3 antibody OKT and a humanized variable region of the heavy chain (5H) of an anti-human EGF receptor 1 antibody 528 in this order from its N-end to C-end.

4. A bispecific antibody of claim 3 wherein the 5L, 5H, OL and OH have an amino acid sequence of SEQ ID NO: 2, 4, 6 and 8, respectively.

5. A pharmaceutical composition comprising the bispecific antibody of claim 3 as an active ingredient, and a pharmaceutically acceptable carrier.

6. The diabody-type bispecific antibody of claim 3, wherein the first polypeptide and the second polypeptide are separate polypeptide chains, and wherein the first polypeptide and second polypeptide are expressed in *E. coli* at their final length.

7. A humanized highly functional bispecific antibody comprising humanized variable regions of the heavy chain (5H) and the light chain (5L) of an anti-human EGF receptor 1 antibody 528, and humanized variable regions of the heavy chain (OH) and the light chain (OL) of an anti-CD3 antibody OKT3; and having the following structure:
  a humanized diabody-type bispecific antibody consisting of two kinds of the single-chain polypeptides of (5LOH) and (OL5H) is bonded to two Fc regions of a human antibody via each hinge region through either of the two single-chain polypeptides.

8. The humanized highly functional bispecific antibody of claim 7, wherein the humanized diabody-type bispecific antibody is bonded to the hinge regions via a protease cleavage site.

9. A bispecific antibody of claim 7 wherein the 5L, 5H, OL and OH have an amino acid sequence of SEQ ID NO: 2, 4, 6 and 8, respectively.

10. The diabody-type bispecific antibody of claim 3 or 7 wherein the humanized variable region of the light chain and the humanized variable region of the heavy chain are linked via a peptide linker in the single-chain polypeptide.

11. A method for inhibiting or reducing tumor cells in a subject, comprising:
  administering to the subject composition of claim 5 in an effective amount to inhibit or reduce tumor cells.

* * * * *

SEQUENCE LISTING

```
<160> NUMBER OF SEQ ID NOS: 18

<210> SEQ ID NO 1
<211> LENGTH: 339
<212> TYPE: DNA
<213> ORGANISM: Artificial Sequence
<220> FEATURE:
<223> OTHER INFORMATION: Chimeric Sequence (h5L)
<220> FEATURE:
<221> NAME/KEY: CDS
<222> LOCATION: (1)..(339)
<223> OTHER INFORMATION:

<400> SEQUENCE: 1 gat att gtg atg acc cag agc ccg ctg agc ctg ccg gtg acc cca ggc      48
Asp Ile Val Met Thr Gln Ser Pro Leu Ser Leu Pro Val Thr Pro Gly
1               5                   10                  15 gaa ccg gcg tcg att agc tgc cgc agc tcg cag aac atc gtg cat aat      96
Glu Pro Ala Ser Ile Ser Cys Arg Ser Ser Gln Asn Ile Val His Asn
                20                  25                  30 aac ggc att acc tat ctg gaa tgg tat ctg cag aaa ccg ggc caa agc     144
Asn Gly Ile Thr Tyr Leu Glu Trp Tyr Leu Gln Lys Pro Gly Gln Ser
            35                  40                  45 ccg cag ctg tta att tat aaa gtg agc gat cgc ttt agc ggc gtg ccg     192
Pro Gln Leu Leu Ile Tyr Lys Val Ser Asp Arg Phe Ser Gly Val Pro
        50                  55                  60 gat cgc ttt tcg ggc agc ggt agt ggc acc gat ttt acg ctg aaa att     240
Asp Arg Phe Ser Gly Ser Gly Ser Gly Thr Asp Phe Thr Leu Lys Ile
65                  70                  75                  80 agc cgc gtg gaa gcg gag gat gtt ggc gtg tat tac tgc ttt cag ggc     288
Ser Arg Val Glu Ala Glu Asp Val Gly Val Tyr Tyr Cys Phe Gln Gly
                85                  90                  95 agc cat atc ccg cca acc ttt ggc caa ggc acc aaa gtg gaa att aaa     336
Ser His Ile Pro Pro Thr Phe Gly Gln Gly Thr Lys Val Glu Ile Lys
                100                 105                 110 cgc                                                                 339
Arg

<210> SEQ ID NO 2
<211> LENGTH: 113
<212> TYPE: PRT
<213> ORGANISM: Artificial Sequence
<220> FEATURE:
<223> OTHER INFORMATION: Chimeric Sequence (h5L)

<400> SEQUENCE: 2

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Asn Ile Val His Asn
                20                  25                  30

Asn Gly Ile Thr Tyr Leu Glu Trp Tyr Leu Gln Lys Pro Gly Gln Ser
            35                  40                  45

Pro Gln Leu Leu Ile Tyr Lys Val Ser Asp Arg Phe Ser Gly Val Pro
```

```
                50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Ile Pro Pro Thr Phe Gly Gln Gly Thr Lys Val Glu Ile Lys
                100                 105                 110

Arg
```

```
<210> SEQ ID NO 3
<211> LENGTH: 354
<212> TYPE: DNA
<213> ORGANISM: Artificial Sequence
<220> FEATURE:
<223> OTHER INFORMATION: Chimeric Sequence (h5H)
<220> FEATURE:
<221> NAME/KEY: CDS
<222> LOCATION: (1)..(354)
<223> OTHER INFORMATION:

<400> SEQUENCE: 3
```

```
cag gtg caa ctg gtt cag agc ggc gcg gaa gtg aaa aag ccg ggc gcg    48
Gln Val Gln Leu Val Gln Ser Gly Ala Glu Val Lys Lys Pro Gly Ala
 1               5                  10                  15 tcg gtt aaa gtg agc tgc aaa gcc tca ggc tat acc ttt acg agc tac    96
Ser Val Lys Val Ser Cys Lys Ala Ser Gly Tyr Thr Phe Thr Ser Tyr
                20                  25                  30 tgg atg cat tgg gtg cgc cag gcc ccg ggt cag ggc ctg gaa tgg atg   144
Trp Met His Trp Val Arg Gln Ala Pro Gly Gln Gly Leu Glu Trp Met
            35                  40                  45 ggt aac att tat ccg ggc agc ggt ggc acc aac tat gcg gaa aaa ttt   192
Gly Asn Ile Tyr Pro Gly Ser Gly Gly Thr Asn Tyr Ala Glu Lys Phe
 50                  55                  60 aag aac cgc gtg acc atg acg cgt gat acc agc att tcg acg gcc tat   240
Lys Asn Arg Val Thr Met Thr Arg Asp Thr Ser Ile Ser Thr Ala Tyr
 65                  70                  75                  80 atg gaa ctg agc cgc ctg cgt agc gat gac acc gcc gtg tat tac tgc   288
Met Glu Leu Ser Arg Leu Arg Ser Asp Asp Thr Ala Val Tyr Tyr Cys
                 85                  90                  95 gcg cgc agt ggc ggt ccg tat ttt ttc gat tac tgg ggc cag ggt acg   336
Ala Arg Ser Gly Gly Pro Tyr Phe Phe Asp Tyr Trp Gly Gln Gly Thr
                100                 105                 110 ctg gtt acc gtg agc tcg                                            354
Leu Val Thr Val Ser Ser
            115
```

```
<210> SEQ ID NO 4
<211> LENGTH: 118
<212> TYPE: PRT
<213> ORGANISM: Artificial Sequence
<220> FEATURE:
<223> OTHER INFORMATION: Chimeric Sequence (h5H)

<400> SEQUENCE: 4
```

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Asn Ile Tyr Pro Gly Ser Gly Gly Thr Asn Tyr Ala Glu Lys Phe
```

```
                    50                  55                  60
Lys Asn Arg Val Thr Met Thr Arg Asp Thr Ser Ile Ser Thr Ala Tyr
 65                  70                  75                  80

Met Glu Leu Ser Arg Leu Arg Ser Asp Thr Ala Val Tyr Tyr Cys
                 85                  90                  95

Ala Arg Ser Gly Gly Pro Tyr Phe Phe Asp Tyr Trp Gly Gln Gly Thr
            100                 105                 110

Leu Val Thr Val Ser Ser
            115

<210> SEQ ID NO 5
<211> LENGTH: 321
<212> TYPE: DNA
<213> ORGANISM: Artificial Sequence
<220> FEATURE:
<223> OTHER INFORMATION: Chimeric Sequence (hOL)
<220> FEATURE:
<221> NAME/KEY: CDS
<222> LOCATION: (1)..(321)
<223> OTHER INFORMATION:

<400> SEQUENCE: 5 gat atc cag atg acc cag agc ccg agc tct ctg agc gcg agc gtg ggc    48
Asp Ile Gln Met Thr Gln Ser Pro Ser Ser Leu Ser Ala Ser Val Gly
 1               5                  10                  15 gat cgc gtg acc att acg tgc agc gcg tct agc tct gtg agc tat atg    96
Asp Arg Val Thr Ile Thr Cys Ser Ala Ser Ser Ser Val Ser Tyr Met
             20                  25                  30 aac tgg tac cag caa acc cca ggc aaa gcg ccg aaa cgc tgg att tat   144
Asn Trp Tyr Gln Gln Thr Pro Gly Lys Ala Pro Lys Arg Trp Ile Tyr
         35                  40                  45 gat acc agc aaa ctg gcg agc ggc gtg ccg agc cgc ttt agc ggc tct   192
Asp Thr Ser Lys Leu Ala Ser Gly Val Pro Ser Arg Phe Ser Gly Ser
     50                  55                  60 ggt agc ggc acc gat tat acg ttt acc att agc tct ctg cag ccg gaa   240
Gly Ser Gly Thr Asp Tyr Thr Phe Thr Ile Ser Ser Leu Gln Pro Glu
 65                  70                  75                  80 gat att gcg acc tat tac tgc cag caa tgg agc tct aac ccg ttt acc   288
Asp Ile Ala Thr Tyr Tyr Cys Gln Gln Trp Ser Ser Asn Pro Phe Thr
             85                  90                  95 ttt ggc cag ggt acc aaa ctg cag att acc cgc                       321
Phe Gly Gln Gly Thr Lys Leu Gln Ile Thr Arg
            100                 105

<210> SEQ ID NO 6
<211> LENGTH: 107
<212> TYPE: PRT
<213> ORGANISM: Artificial Sequence
<220> FEATURE:
<223> OTHER INFORMATION: Chimeric Sequence (hOL)

<400> SEQUENCE: 6

Asp Ile Gln Met Thr Gln Ser Pro Ser Ser Leu Ser Ala Ser Val Gly
 1               5                  10                  15

Asp Arg Val Thr Ile Thr Cys Ser Ala Ser Ser Ser Val Ser Tyr Met
             20                  25                  30

Asn Trp Tyr Gln Gln Thr Pro Gly Lys Ala Pro Lys Arg Trp Ile Tyr
         35                  40                  45

Asp Thr Ser Lys Leu Ala Ser Gly Val Pro Ser Arg Phe Ser Gly Ser
     50                  55                  60

Gly Ser Gly Thr Asp Tyr Thr Phe Thr Ile Ser Ser Leu Gln Pro Glu
```

```
                    65                  70                  75                  80
Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr Arg
            100                 105

<210> SEQ ID NO 7
<211> LENGTH: 357
<212> TYPE: DNA
<213> ORGANISM: Artificial Sequence
<220> FEATURE:
<223> OTHER INFORMATION: Chimeric Sequence (hOH)
<220> FEATURE:
<221> NAME/KEY: CDS
<222> LOCATION: (1)..(357)
<223> OTHER INFORMATION:

<400> SEQUENCE: 7 cag gtg caa ctg gtg cag agc ggc ggt ggc gtt gtg cag ccg ggc cgc       48
Gln Val Gln Leu Val Gln Ser Gly Gly Gly Val Val Gln Pro Gly Arg
1               5                   10                  15 agc ctg cgc ctg tct tgc aaa gcg agc ggc tat acc ttt acg cgc tat       96
Ser Leu Arg Leu Ser Cys Lys Ala Ser Gly Tyr Thr Phe Thr Arg Tyr
                20                  25                  30 acc atg cat tgg gtg cgc cag gcg ccg ggc aaa ggt ctg gaa tgg att      144
Thr Met His Trp Val Arg Gln Ala Pro Gly Lys Gly Leu Glu Trp Ile
            35                  40                  45 ggc tat att aac ccg tct cgc ggc tat acc aac tat aat cag aaa gtg      192
Gly Tyr Ile Asn Pro Ser Arg Gly Tyr Thr Asn Tyr Asn Gln Lys Val
        50                  55                  60 aaa gat cgc ttt acc att agc cgc gat aac tct aaa aac acc gcg ttt      240
Lys Asp Arg Phe Thr Ile Ser Arg Asp Asn Ser Lys Asn Thr Ala Phe
65                  70                  75                  80 ctg cag atg gat agc ctg cgc ccg gaa gat acc ggc gtg tat ttt tgc      288
Leu Gln Met Asp Ser Leu Arg Pro Glu Asp Thr Gly Val Tyr Phe Cys
                85                  90                  95 gcg cgc tac tat gat gac cat tat agc ctg gat tat tgg ggc cag ggc      336
Ala Arg Tyr Tyr Asp Asp His Tyr Ser Leu Asp Tyr Trp Gly Gln Gly
                100                 105                 110 acc ccg gtg acc gtt agc tcg                                          357
Thr Pro Val Thr Val Ser Ser
            115

<210> SEQ ID NO 8
<211> LENGTH: 119
<212> TYPE: PRT
<213> ORGANISM: Artificial Sequence
<220> FEATURE:
<223> OTHER INFORMATION: Chimeric Sequence (hOH)

<400> SEQUENCE: 8

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
                20                  25                  30

Thr Met His Trp Val Arg Gln Ala Pro Gly Lys Gly Leu Glu Trp Ile
            35                  40                  45

Gly Tyr Ile Asn Pro Ser Arg Gly Tyr Thr Asn Tyr Asn Gln Lys Val
        50                  55                  60

Lys Asp Arg Phe Thr Ile Ser Arg Asp Asn Ser Lys Asn Thr Ala Phe
65                  70                  75                  80
```

```
                Leu Gln Met Asp Ser Leu Arg Pro Glu Asp Thr Gly Val Tyr Phe Cys
                             85                  90                  95

Ala Arg Tyr Tyr Asp Asp His Tyr Ser Leu Asp Tyr Trp Gly Gln Gly
                        100                 105                 110

Thr Pro Val Thr Val Ser Ser
                        115

<210> SEQ ID NO 9
<211> LENGTH: 36
<212> TYPE: DNA
<213> ORGANISM: Artificial Sequence
<220> FEATURE:
<223> OTHER INFORMATION: NcoI-5L
<220> FEATURE:
<221> NAME/KEY: misc_feature
<222> LOCATION: (1)..(4)
<223> OTHER INFORMATION: Any

<400> SEQUENCE: 9
nnnnccatgg ccgatattgt gatgacccag agcccg                                   36

<210> SEQ ID NO 10
<211> LENGTH: 45
<212> TYPE: DNA
<213> ORGANISM: Artificial Sequence
<220> FEATURE:
<223> OTHER INFORMATION: 5LSG4

<400> SEQUENCE: 10
ctggccaccg ccaccagatt taatttccac tttggtgcca ccgcc                         45

<210> SEQ ID NO 11
<211> LENGTH: 42
<212> TYPE: DNA
<213> ORGANISM: Artificial Sequence
<220> FEATURE:
<223> OTHER INFORMATION: SG4OH

<400> SEQUENCE: 11
aaatctggtg gcggtggcca ggtgcaactg gtgcagagcg gc                            42

<210> SEQ ID NO 12
<211> LENGTH: 40
<212> TYPE: DNA
<213> ORGANISM: Artificial Sequence
<220> FEATURE:
<223> OTHER INFORMATION: OH-SacII
<220> FEATURE:
<221> NAME/KEY: misc_feature
<222> LOCATION: (1)..(4)
<223> OTHER INFORMATION: Any

<400> SEQUENCE: 12
nnnnagccgc ggagctaacg gtcaccgggg tgccctggcc                               40

<210> SEQ ID NO 13
<211> LENGTH: 36
<212> TYPE: DNA
<213> ORGANISM: Artificial Sequence
<220> FEATURE:
<223> OTHER INFORMATION: NcoI-OL
<220> FEATURE:
<221> NAME/KEY: misc_feature
<222> LOCATION: (1)..(4)
<223> OTHER INFORMATION: Any

<400> SEQUENCE: 13
```

-continued

```
nnnnccatgg ccgatattca gatgacccag agcccg                                36

<210> SEQ ID NO 14
<211> LENGTH: 42
<212> TYPE: DNA
<213> ORGANISM: Artificial Sequence
<220> FEATURE:
<223> OTHER INFORMATION: OLSG4

<400> SEQUENCE: 14
ctggccaccg ccaccagagg taatctgcag tttggtaccc tg                         42

<210> SEQ ID NO 15
<211> LENGTH: 42
<212> TYPE: DNA
<213> ORGANISM: Artificial Sequence
<220> FEATURE:
<223> OTHER INFORMATION: SG45H

<400> SEQUENCE: 15
acctctggtg gcggtggcca ggtgcaactg gttcagagcg gc                         42

<210> SEQ ID NO 16
<211> LENGTH: 34
<212> TYPE: DNA
<213> ORGANISM: Artificial Sequence
<220> FEATURE:
<223> OTHER INFORMATION: 5H-Sac II
<220> FEATURE:
<221> NAME/KEY: misc_feature
<222> LOCATION: (1)..(4)
<223> OTHER INFORMATION: Any

<400> SEQUENCE: 16
nnnnagccgc ggagctcacg gtaaccagcg tacc                                  34

<210> SEQ ID NO 17
<211> LENGTH: 30
<212> TYPE: DNA
<213> ORGANISM: Artificial Sequence
<220> FEATURE:
<223> OTHER INFORMATION: SpeI-pel-B

<400> SEQUENCE: 17
actagttatt tcaaggagac agtcataatg                                       30

<210> SEQ ID NO 18
<211> LENGTH: 31
<212> TYPE: DNA
<213> ORGANISM: Artificial Sequence
<220> FEATURE:
<223> OTHER INFORMATION: His-BamHI

<400> SEQUENCE: 18
caccatcatc accaccatta atagcggatt c                                     31
```